US007611873B1

(12) United States Patent
Usuda et al.

(10) Patent No.: US 7,611,873 B1
(45) Date of Patent: Nov. 3, 2009

(54) METHOD FOR PRODUCING L-METHIONINE BY FERMENTATION

(75) Inventors: Yoshihiro Usuda, Kawasaki (JP); Osamu Kurahashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/441,055

(22) Filed: Nov. 16, 1999

(30) Foreign Application Priority Data

Nov. 17, 1998 (JP) ................................. 10-326717

(51) Int. Cl.
  C12P 13/12    (2006.01)
  C12P 13/04    (2006.01)
  C12N 9/00     (2006.01)
  C12N 9/10     (2006.01)
  C12N 1/20     (2006.01)
  C12N 15/00    (2006.01)
  C07H 21/04    (2006.01)

(52) U.S. Cl. ...................... 435/113; 435/106; 435/183; 435/193; 435/252.3; 435/320.1; 536/23.2

(58) Field of Classification Search ................. 435/106, 435/113, 243, 252.1, 252.3, 183, 193, 320.1, 435/320; 536/23.2
See application file for complete search history.

(56) References Cited

FOREIGN PATENT DOCUMENTS

JP       49-35580     4/1974
JP       56-35992     4/1981

OTHER PUBLICATIONS

Michaeli et al. (Advances in Polyamine Research (1983), 4, 519-20.*
Park et al. Bioorg Med Chem. Dec. 1996;4(12):2179-85.*
Parsot et al. Mol Microbiol. Jul. 1987;1(1):45-52.*
Malumbres et al. Appl Environ Microbiol. Jul. 1994;60(7):2209-19.*
Michaeli et al. Advances in Polyamine Research (1983), 4, 519-20.*
L.-W. Lee, et al., Journal of Biological Chemistry, vol. 241, No. 22, pp. 5479-5480, "Multimetabolite Control of a Biosynethetic Pathway by Sequential Metabolites", 1966.
B. Duclos, et al., Nucleic Acids Research, vol. 17, No. 7, p. 2856, "Nucleotide Sequence of the *metA* Gene Encoding Homoserine *Trans*-Succinylase in *Escherichia coli*", 1989.
M. K. Chattopadhyay, et al., Journal of General Microbiology, vol. 137, pp. 685-691, "Control of Methionine Biosynthesis in *Escherichia coli* K12: A Closer Study With Analogue-Resistant Mutants", 1991.
D. A. Lawrence, Journal of Bacteriology, vol. 109, No. 1, pp. 8-11, "Regulation of the Methionine Feedback-Sensitive Enzyme in Mutants of *Salmonella typhimurium*", 1972.
R. C. Greene, *Escherichia coli* and *Salmonella* Cellular and Molecular Biology, 2nd Edition, pp. 542-560, "Biosynthesis of Methionine", 1996.
N. Duchange, et al., Journal of Biological Chemistry, vol. 258, No. 24, pp. 14868-14871, "Structure of the *metJBLF* Cluster in *Escherichia coli* K12: Sequence of the *metB* Structural Gene and of the 5'-and 3'-Flanking Regions of the *metBL* Operon", 1983.

R.C. Greene, et al., Journal of Bacteriology, vol. 115, No. 1, pp. 57-67, "Properties of *metK* Mutants of *Escherichia coli* K12", 1973.
M.M. Zakin, et al., "Nucleotide Sequence of the METL Gene of *Escherichia coli*", The Journal of Biological Chemistry, vol. 258, No. 5, Mar. 10, 1983, pp. 3028-3031.
N. Duchange, et al., "Structure of the ETJBLF Cluster in *Escherichia coli* K12", The Journal of Biological Chemistry, vol. 258, No. 24, Dec. 25, 1983, pp. 14868-14871.
Frederick R. Blattner, et al., "The Complete Genome Sequence of *Escherichia coli* K-12", Science, 1997, vol. 277, pp. 1453-1462.
Thomas W. Kirby, et al, "Regulation of in Vivo Transcription of the *Escherichia coli* K-12 metJBLF Gene Cluster", Journal of Bacteriology, vol. 165, No. 3, Mar. 1986, pp. 671-677.
J. Thèze , et al., "Threonine Locus of *Escherichia coil* K-12: Genetic Structure and Evidence for an Operon". Journal of Bacteriology, vol. 118, No. 3, Jun. 1974, pp. 990-998.
Jeffrey F. Gardner, Initiation, Pausing, and Termination of Transcription in the Threonine Operon Regulatory Region of *Escherichia coli*, The Journal of Biological Chemistry, vol. 257, No. 7, Apr. 10, 1982, pp. 3896-3904.
M.L. Urbanowski, et al., "Autoregulation by Tandem Promoters of the Salmonella Typhimurium LT2 metJ Gene", Journal of Bacteriology, vol. 165, No. 3, Mar. 1986, pp. 740-745.
R. Mares, et al., "Regulation of the Salmonella Typhimurium metA Gene by the metR Protein and Homocysteine", Journal of Bacteriology, vol. 174, No. 2, Jan. 1992, pp. 390-397.
R.R. Yocum, et al., "Cloning and Characterization of the metE Gene Encoding Sadenosylmethionine Synthetase From Bacillus Subtilis", Journal of Bacteriology, vol. 178, No. 15, Aug. 1996, pp. 4604-4610.
K. Omori, et al., "Nucleotide Sequence of the Serratia Marcescens Threonine Operon and Analysis of the Threonine Operon Mutations Which Alter Feedback Inhibition of Both Aspartokinase I and Homoserine Dehydrogenase I", Journal of Bacteriology, vol. 175, No. 3, Feb. 1993, pp. 785-794.
M.L. Urbanowski, et al., "Cloning and Initial Characterization of the metJ and metB Genes From Salmonella Typhimurium LT2", Gene, 35 (1985), pp. 187-197.

* cited by examiner

*Primary Examiner*—Christian L Fronda
(74) *Attorney, Agent, or Firm*—Oblon, Spivak, McClelland, Maier & Neustadt, L.L.P.

(57) ABSTRACT

L-Methionine is produced by culturing a microorganism which is deficient in repressor of L-methionine biosynthesis system and/or enhanced intracellular homoserine transsuccinylase activity is cultured in a medium so that L-methionine should be produced and accumulated in the medium, and collecting the L-methionine from the medium. The microorganism preferably further exhibits reduced intracellular S-adenosylmethionine synthetase activity, L-threonine auxotrophy, enhanced intracellular cystathionine γ-synthase activity and enhanced intracellular aspartokinase-homoserine dehydrogenase II activity. The present invention enables breeding of L-methionine-producing bacteria, and L-methionine production by fermentation.

21 Claims, No Drawings

SEQUENCE LISTING

<160> NUMBER OF SEQ ID NOS: 29

<210> SEQ ID NO 1
<211> LENGTH: 28
<212> TYPE: DNA
<213> ORGANISM: Artificial Sequence
<220> FEATURE:
<223> OTHER INFORMATION: Synthetic DNA

<400> SEQUENCE: 1
gggaattctg gcaggaggaa ctggcgca                28

<210> SEQ ID NO 2
<211> LENGTH: 28
<212> TYPE: DNA
<213> ORGANISM: Artificial Sequence
<220> FEATURE:
<223> OTHER INFORMATION: Synthetic DNA

<400> SEQUENCE: 2
gggtcgacgc tcatattggc actggaag                           28

<210> SEQ ID NO 3
<211> LENGTH: 28
<212> TYPE: DNA
<213> ORGANISM: Artificial Sequence
<220> FEATURE:
<223> OTHER INFORMATION: Synthetic DNA

<400> SEQUENCE: 3
gggtcgacat cagtaaaatc tattcatt                           28

<210> SEQ ID NO 4
<211> LENGTH: 28
<212> TYPE: DNA
<213> ORGANISM: Artificial Sequence
<220> FEATURE:
<223> OTHER INFORMATION: Synthetic DNA

<400> SEQUENCE: 4
ggaagcttgc ccgagggaaa gatctgta                           28

<210> SEQ ID NO 5
<211> LENGTH: 28
<212> TYPE: DNA
<213> ORGANISM: Artificial Sequence
<220> FEATURE:
<223> OTHER INFORMATION: Synthetic DNA

<400> SEQUENCE: 5
gggcatgccc agggaacttc atcacatg                           28

<210> SEQ ID NO 6
<211> LENGTH: 28
<212> TYPE: DNA
<213> ORGANISM: Artificial Sequence
<220> FEATURE:
<223> OTHER INFORMATION: Synthetic DNA

<400> SEQUENCE: 6
gggaattctc atggttgcgg cgtgagag                           28

<210> SEQ ID NO 7
<211> LENGTH: 28
<212> TYPE: DNA
<213> ORGANISM: Artificial Sequence
<220> FEATURE:
<223> OTHER INFORMATION: Synthetic DNA

<400> SEQUENCE: 7
ggaagcttgc gtgagatggg gattaacc                           28

<210> SEQ ID NO 8
<211> LENGTH: 28
<212> TYPE: DNA
<213> ORGANISM: Artificial Sequence
<220> FEATURE:
<223> OTHER INFORMATION: Synthetic DNA

<400> SEQUENCE: 8
gggaattcta ctgctagctg ctcttgcg                           28

<210> SEQ ID NO 9
<211> LENGTH: 75
<212> TYPE: DNA

<213> ORGANISM: Artificial Sequence
<220> FEATURE:
<223> OTHER INFORMATION: Synthetic DNA

<400> SEQUENCE: 9

```
ggaagcttaa aatttattg acttaggtca ctaaatactt taaccaatat aggcatagcg    60
cacagacgca tgccc                                                    75
```

<210> SEQ ID NO 10
<211> LENGTH: 75
<212> TYPE: DNA
<213> ORGANISM: Artificial Sequence
<220> FEATURE:
<223> OTHER INFORMATION: Synthetic DNA

<400> SEQUENCE: 10

```
gggcatgcgt ctgtgcgcta tgcctatatt ggttaaagta tttagtgacc taagtcaata    60
aaattttaag cttcc                                                    75
```

<210> SEQ ID NO 11
<211> LENGTH: 18
<212> TYPE: DNA
<213> ORGANISM: Artificial Sequence
<220> FEATURE:
<223> OTHER INFORMATION: Synthetic DNA

<400> SEQUENCE: 11

```
caacagtttg agctaacc                                                 18
```

<210> SEQ ID NO 12
<211> LENGTH: 20
<212> TYPE: DNA
<213> ORGANISM: Artificial Sequence
<220> FEATURE:
<223> OTHER INFORMATION: Synthetic DNA

<400> SEQUENCE: 12

```
gcggttttt tgccggatgc                                                20
```

<210> SEQ ID NO 13
<211> LENGTH: 18
<212> TYPE: DNA
<213> ORGANISM: Artificial Sequence
<220> FEATURE:
<223> OTHER INFORMATION: Synthetic DNA

<400> SEQUENCE: 13

```
tcggctacgc aactaatg                                                 18
```

<210> SEQ ID NO 14
<211> LENGTH: 18
<212> TYPE: DNA
<213> ORGANISM: Artificial Sequence
<220> FEATURE:
<223> OTHER INFORMATION: Synthetic DNA

<400> SEQUENCE: 14

```
gagaatgcac cgccaccg                                                 18
```

<210> SEQ ID NO 15
<211> LENGTH: 18
<212> TYPE: DNA
<213> ORGANISM: Artificial Sequence
<220> FEATURE:
<223> OTHER INFORMATION: Synthetic DNA -continued

```
<400> SEQUENCE: 15
tggcgcgtca cggtggcg                                                   18

<210> SEQ ID NO 16
<211> LENGTH: 18
<212> TYPE: DNA
<213> ORGANISM: Artificial Sequence
<220> FEATURE:
<223> OTHER INFORMATION: Synthetic DNA

<400> SEQUENCE: 16
gcacgtcggt ttcattag                                                   18

<210> SEQ ID NO 17
<211> LENGTH: 1155
<212> TYPE: DNA
<213> ORGANISM: Escherichia coli
<220> FEATURE:
<221> NAME/KEY: CDS
<222> LOCATION: (1)..(1152)
<223> OTHER INFORMATION:

<400> SEQUENCE: 17 atg gca aaa cac ctt ttt acg tcc gag tcc gtc tct gaa ggg cat cct      48
Met Ala Lys His Leu Phe Thr Ser Glu Ser Val Ser Glu Gly His Pro
1               5                   10                  15 gac aaa att gct gac caa att tct gat gcc gtt tta gac gcg atc ctc      96
Asp Lys Ile Ala Asp Gln Ile Ser Asp Ala Val Leu Asp Ala Ile Leu
            20                  25                  30 gaa cag gat ccg aaa gca cgc gtt gct tgc gaa acc tac gta aaa acc     144
Glu Gln Asp Pro Lys Ala Arg Val Ala Cys Glu Thr Tyr Val Lys Thr
        35                  40                  45 ggc atg gtt tta gtt ggc ggc gaa atc acc acc agc gcc tgg gta gac     192
Gly Met Val Leu Val Gly Gly Glu Ile Thr Thr Ser Ala Trp Val Asp
    50                  55                  60 atc gaa gag atc acc cgt aac acc gtt cgc gaa att ggc tat gtg cat     240
Ile Glu Glu Ile Thr Arg Asn Thr Val Arg Glu Ile Gly Tyr Val His
65                  70                  75                  80 tcc gac atg ggc ttt gac gct aac tcc tgt gcg gtt ctg agc gct atc     288
Ser Asp Met Gly Phe Asp Ala Asn Ser Cys Ala Val Leu Ser Ala Ile
                85                  90                  95 ggc aaa cag tct cct gac atc aac cag ggc gtt gac cgt gcc gat ccg     336
Gly Lys Gln Ser Pro Asp Ile Asn Gln Gly Val Asp Arg Ala Asp Pro
            100                 105                 110 ctg gaa cag ggc gcg ggt gac cag ggt ctg atg ttt ggc tac gca act     384
Leu Glu Gln Gly Ala Gly Asp Gln Gly Leu Met Phe Gly Tyr Ala Thr
        115                 120                 125 aat gaa acc gac gtg ctg atg cca gca cct atc acc tat gca cac cgt     432
Asn Glu Thr Asp Val Leu Met Pro Ala Pro Ile Thr Tyr Ala His Arg
    130                 135                 140 ctg gta cag cgt cag gct gaa gtg cgt aaa aac ggc act ctg ccg tgg     480
Leu Val Gln Arg Gln Ala Glu Val Arg Lys Asn Gly Thr Leu Pro Trp
145                 150                 155                 160 ctg cgc ccg gac gcg aaa agc cag gtg act ttt cag tat gac gac ggc     528
Leu Arg Pro Asp Ala Lys Ser Gln Val Thr Phe Gln Tyr Asp Asp Gly
                165                 170                 175 aaa atc gtt ggt atc gat gct gtc gtg ctt tcc act cag cac tct gaa     576
Lys Ile Val Gly Ile Asp Ala Val Val Leu Ser Thr Gln His Ser Glu
            180                 185                 190 gag atc gac cag aaa tcg ctg caa gaa gcg gta atg gaa gag atc atc     624
Glu Ile Asp Gln Lys Ser Leu Gln Glu Ala Val Met Glu Glu Ile Ile
        195                 200                 205
```

```
aag cca att ctg ccc gct gaa tgg ctg act tct gcc acc aaa ttc ttc    672
Lys Pro Ile Leu Pro Ala Glu Trp Leu Thr Ser Ala Thr Lys Phe Phe
    210                 215                 220 atc aac ccg acc ggt cgt ttc gtt atc ggt ggc cca atg ggt gac tgc    720
Ile Asn Pro Thr Gly Arg Phe Val Ile Gly Gly Pro Met Gly Asp Cys
225                 230                 235                 240 ggt ctg act ggt cgt aaa atc atc gtt gat acc tac ggc ggc atg gcg    768
Gly Leu Thr Gly Arg Lys Ile Ile Val Asp Thr Tyr Gly Gly Met Ala
            245                 250                 255 cgt cac ggt ggc ggt gca ttc tct ggt aaa gat cca tca aaa gtg gac    816
Arg His Gly Gly Gly Ala Phe Ser Gly Lys Asp Pro Ser Lys Val Asp
        260                 265                 270 cgt tcc gca gcc tac gca gca cgt tat gtc gcg aaa aac atc gtt gct    864
Arg Ser Ala Ala Tyr Ala Ala Arg Tyr Val Ala Lys Asn Ile Val Ala
    275                 280                 285 gct ggc ctg gcc gat cgt tgt gaa att cag gtt tcc tac gca atc ggc    912
Ala Gly Leu Ala Asp Arg Cys Glu Ile Gln Val Ser Tyr Ala Ile Gly
290                 295                 300 gtg gct gaa ccg acc tcc atc atg gta gaa act ttc ggt act gag aaa    960
Val Ala Glu Pro Thr Ser Ile Met Val Glu Thr Phe Gly Thr Glu Lys
305                 310                 315                 320 gtg cct tct gaa caa ctg acc ctg ctg gta cgt gag ttc ttc gac ctg   1008
Val Pro Ser Glu Gln Leu Thr Leu Leu Val Arg Glu Phe Phe Asp Leu
            325                 330                 335 cgc cca tac ggt ctg att cag atg ctg gat ctg ctg cac ccg atc tac   1056
Arg Pro Tyr Gly Leu Ile Gln Met Leu Asp Leu Leu His Pro Ile Tyr
        340                 345                 350 aaa gaa acc gca gca tac ggt cac ttt ggt cgt gaa cat ttc ccg tgg   1104
Lys Glu Thr Ala Ala Tyr Gly His Phe Gly Arg Glu His Phe Pro Trp
    355                 360                 365 gaa aaa acc gac aaa gcg cag ctg ctg cgc gat gct gcc ggt ctg aag   1152
Glu Lys Thr Asp Lys Ala Gln Leu Leu Arg Asp Ala Ala Gly Leu Lys
370                 375                 380 taa                                                                1155
```

<210> SEQ ID NO 18
<211> LENGTH: 384
<212> TYPE: PRT
<213> ORGANISM: Escherichia coli

<400> SEQUENCE: 18

```
Met Ala Lys His Leu Phe Thr Ser Glu Ser Val Ser Glu Gly His Pro
1               5                   10                  15

Asp Lys Ile Ala Asp Gln Ile Ser Asp Ala Val Leu Asp Ala Ile Leu
            20                  25                  30

Glu Gln Asp Pro Lys Ala Arg Val Ala Cys Glu Thr Tyr Val Lys Thr
        35                  40                  45

Gly Met Val Leu Val Gly Gly Glu Ile Thr Thr Ser Ala Trp Val Asp
    50                  55                  60

Ile Glu Glu Ile Thr Arg Asn Thr Val Arg Glu Ile Gly Tyr Val His
65                  70                  75                  80

Ser Asp Met Gly Phe Asp Ala Asn Ser Cys Ala Val Leu Ser Ala Ile
                85                  90                  95

Gly Lys Gln Ser Pro Asp Ile Asn Gln Gly Val Asp Arg Ala Asp Pro
            100                 105                 110

Leu Glu Gln Gly Ala Gly Asp Gln Gly Leu Met Phe Gly Tyr Ala Thr
        115                 120                 125

Asn Glu Thr Asp Val Leu Met Pro Ala Pro Ile Thr Tyr Ala His Arg
    130                 135                 140
```

```
Leu Val Gln Arg Gln Ala Glu Val Arg Lys Asn Gly Thr Leu Pro Trp
145                 150                 155                 160

Leu Arg Pro Asp Ala Lys Ser Gln Val Thr Phe Gln Tyr Asp Asp Gly
            165                 170                 175

Lys Ile Val Gly Ile Asp Ala Val Val Leu Ser Thr Gln His Ser Glu
        180                 185                 190

Glu Ile Asp Gln Lys Ser Leu Gln Glu Ala Val Met Glu Glu Ile Ile
    195                 200                 205

Lys Pro Ile Leu Pro Ala Glu Trp Leu Thr Ser Ala Thr Lys Phe Phe
210                 215                 220

Ile Asn Pro Thr Gly Arg Phe Val Ile Gly Pro Met Gly Asp Cys
225                 230                 235                 240

Gly Leu Thr Gly Arg Lys Ile Ile Val Asp Thr Tyr Gly Gly Met Ala
                245                 250                 255

Arg His Gly Gly Gly Ala Phe Ser Gly Lys Asp Pro Ser Lys Val Asp
            260                 265                 270

Arg Ser Ala Ala Tyr Ala Ala Arg Tyr Val Ala Lys Asn Ile Val Ala
        275                 280                 285

Ala Gly Leu Ala Asp Arg Cys Glu Ile Gln Val Ser Tyr Ala Ile Gly
    290                 295                 300

Val Ala Glu Pro Thr Ser Ile Met Val Glu Thr Phe Gly Thr Glu Lys
305                 310                 315                 320

Val Pro Ser Glu Gln Leu Thr Leu Leu Val Arg Glu Phe Phe Asp Leu
                325                 330                 335

Arg Pro Tyr Gly Leu Ile Gln Met Leu Asp Leu Leu His Pro Ile Tyr
            340                 345                 350

Lys Glu Thr Ala Ala Tyr Gly His Phe Gly Arg Glu His Phe Pro Trp
        355                 360                 365

Glu Lys Thr Asp Lys Ala Gln Leu Leu Arg Asp Ala Ala Gly Leu Lys
    370                 375                 380

<210> SEQ ID NO 19
<211> LENGTH: 28
<212> TYPE: DNA
<213> ORGANISM: Artificial Sequence
<220> FEATURE:
<223> OTHER INFORMATION: Synthetic DNA

<400> SEQUENCE: 19
ggaagcttaa gcagagatgc agagtgcg                                    28

<210> SEQ ID NO 20
<211> LENGTH: 28
<212> TYPE: DNA
<213> ORGANISM: Artificial Sequence
<220> FEATURE:
<223> OTHER INFORMATION: Synthetic DNA

<400> SEQUENCE: 20
ggaagcttgg tgcggtataa gaggccac                                    28

<210> SEQ ID NO 21
<211> LENGTH: 28
<212> TYPE: DNA
<213> ORGANISM: Artificial Sequence
<220> FEATURE:
<223> OTHER INFORMATION: Synthetic DNA

<400> SEQUENCE: 21
```

-continued

```
gggcatgctg tagtgaggta atcaggtt                                              28

<210> SEQ ID NO 22
<211> LENGTH: 28
<212> TYPE: DNA
<213> ORGANISM: Artificial Sequence
<220> FEATURE:
<223> OTHER INFORMATION: Synthetic DNA

<400> SEQUENCE: 22
gggtcgactt aatccagcgt tggattca                                              28

<210> SEQ ID NO 23
<211> LENGTH: 18
<212> TYPE: DNA
<213> ORGANISM: Artificial Sequence
<220> FEATURE:
<223> OTHER INFORMATION: Synthetic DNA

<400> SEQUENCE: 23
tgtctgctgg gcggtaca                                                         18

<210> SEQ ID NO 24
<211> LENGTH: 18
<212> TYPE: DNA
<213> ORGANISM: Artificial Sequence
<220> FEATURE:
<223> OTHER INFORMATION: Synthetic DNA

<400> SEQUENCE: 24
agagagtttt tcggtgcg                                                         18

<210> SEQ ID NO 25
<211> LENGTH: 930
<212> TYPE: DNA
<213> ORGANISM: Escherichia coli
<220> FEATURE:
<221> NAME/KEY: CDS
<222> LOCATION: (1)..(927)
<223> OTHER INFORMATION:

<400> SEQUENCE: 25 atg ccg att cgt gtg ccg gac gag cta ccc gcc gtc aat ttc ttg cgt        48
Met Pro Ile Arg Val Pro Asp Glu Leu Pro Ala Val Asn Phe Leu Arg
1               5                   10                  15 gaa gaa aac gtc ttt gtg atg aca act tct cgt gcg tct ggt cag gaa        96
Glu Glu Asn Val Phe Val Met Thr Thr Ser Arg Ala Ser Gly Gln Glu
            20                  25                  30 att cgt cca ctt aag gtt ctg atc ctt aac ctg atg ccg aag aag att       144
Ile Arg Pro Leu Lys Val Leu Ile Leu Asn Leu Met Pro Lys Lys Ile
        35                  40                  45 gaa act gaa aat cag ttt ctg cgc ctg ctt tca aac tca cct ttg cag       192
Glu Thr Glu Asn Gln Phe Leu Arg Leu Leu Ser Asn Ser Pro Leu Gln
    50                  55                  60 gtc gat att cag ctg ttg cgc atc gat tcc cgt gaa tcg cgc aac acg       240
Val Asp Ile Gln Leu Leu Arg Ile Asp Ser Arg Glu Ser Arg Asn Thr
65                  70                  75                  80 ccc gca gag cat ctg aac aac ttc tac tgt aac ttt gaa gat att cag       288
Pro Ala Glu His Leu Asn Asn Phe Tyr Cys Asn Phe Glu Asp Ile Gln
                85                  90                  95 gat cag aac ttt gac ggt ttg att gta act ggt gcg ccg ctg ggc ctg       336
Asp Gln Asn Phe Asp Gly Leu Ile Val Thr Gly Ala Pro Leu Gly Leu
            100                 105                 110
```

```
gtg gag ttt aat gat gtc gct tac tgg ccg cag atc aaa cag gtg ctg        384
Val Glu Phe Asn Asp Val Ala Tyr Trp Pro Gln Ile Lys Gln Val Leu
            115                 120                 125 gag tgg tcg aaa gat cac gtc acc tcg acg ctg ttt gtc tgc tgg gcg        432
Glu Trp Ser Lys Asp His Val Thr Ser Thr Leu Phe Val Cys Trp Ala
130                 135                 140 gta cag gcc gcg ctc aat atc ctc tac ggc att cct aag caa act cgc        480
Val Gln Ala Ala Leu Asn Ile Leu Tyr Gly Ile Pro Lys Gln Thr Arg
145                 150                 155                 160 acc gaa aaa ctc tct ggc gtt tac gag cat cat att ctc cat cct cat        528
Thr Glu Lys Leu Ser Gly Val Tyr Glu His His Ile Leu His Pro His
                165                 170                 175 gcg ctt ctg acg cgt ggc ttt gat gat tca ttc ctg gca ccg cat tcg        576
Ala Leu Leu Thr Arg Gly Phe Asp Asp Ser Phe Leu Ala Pro His Ser
            180                 185                 190 cgc tat gct gac ttt ccg gca gcg ttg att cgt gat tac acc gat ctg        624
Arg Tyr Ala Asp Phe Pro Ala Ala Leu Ile Arg Asp Tyr Thr Asp Leu
        195                 200                 205 gaa att ctg gca gag acg gaa gaa ggg gat gca tat ctg ttt gcc agt        672
Glu Ile Leu Ala Glu Thr Glu Glu Gly Asp Ala Tyr Leu Phe Ala Ser
210                 215                 220 aaa gat aag cgc att gcc ttt gtg acg ggc cat ccc gaa tat gat gcg        720
Lys Asp Lys Arg Ile Ala Phe Val Thr Gly His Pro Glu Tyr Asp Ala
225                 230                 235                 240 caa acg ctg gcg cag gaa ttt ttc cgc gat gtg gaa gcc gga cta gac        768
Gln Thr Leu Ala Gln Glu Phe Phe Arg Asp Val Glu Ala Gly Leu Asp
                245                 250                 255 ccg gat gta ccg tat aac tat ttc ccg cac aat gat ccg caa aat aca        816
Pro Asp Val Pro Tyr Asn Tyr Phe Pro His Asn Asp Pro Gln Asn Thr
            260                 265                 270 ccg cga gcg agc tgg cgt agt cac ggt aat tta ctg ttt acc aac tgg        864
Pro Arg Ala Ser Trp Arg Ser His Gly Asn Leu Leu Phe Thr Asn Trp
        275                 280                 285 ctc aac tat tac gtc tac cag atc acg cca tac gat cta cgg cac atg        912
Leu Asn Tyr Tyr Val Tyr Gln Ile Thr Pro Tyr Asp Leu Arg His Met
290                 295                 300 aat cca acg ctg gat taa                                                930
Asn Pro Thr Leu Asp
305
```

<210> SEQ ID NO 26
<211> LENGTH: 309
<212> TYPE: PRT
<213> ORGANISM: Escherichia coli

<400> SEQUENCE: 26

```
Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95
```

-continued

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
    290                 295                 300

Asn Pro Thr Leu Asp
305

<210> SEQ ID NO 27
<211> LENGTH: 21
<212> TYPE: DNA
<213> ORGANISM: Artificial Sequence
<220> FEATURE:
<223> OTHER INFORMATION: Synthetic DNA

<400> SEQUENCE: 27
ccagacgcac aagaagttgt c                                            21

<210> SEQ ID NO 28
<211> LENGTH: 27
<212> TYPE: DNA
<213> ORGANISM: Artificial Sequence
<220> FEATURE:
<223> OTHER INFORMATION: Synthetic DNA

<400> SEQUENCE: 28
tagatcgtat agcgtgctct ggtagac                                      27

<210> SEQ ID NO 29
<211> LENGTH: 5
<212> TYPE: PRT
<213> ORGANISM: Escherichia coli

<400> SEQUENCE: 29

Ala Met Leu Pro Val
1               5

METHOD FOR PRODUCING L-METHIONINE BY FERMENTATION

TECHNICAL FIELD

The present invention relates to a method for producing L-methionine by fermentation. L-methionine is an important amino acid as a medicament and the like.

BACKGROUND ART

Industrially produced methionine mainly consists of DL-methionine, which is produced through chemical synthesis. When L-methionine is required, it is provided through production of N-acetyl-DL-methionine by acetylation of DL-methionine and subsequent enzymatic selective deacetylation of the N-acetylated L-methionine.

On the other hand, as for the production of L-methionine by fermentation, methods utilizing an L-methionine analogue-resistant mutant strain have been reported. However, their production amount is small, and factors affecting the L-methionine production have not been elucidated yet. Therefore, L-methionine is still one of the amino acids the most difficult to be produced by fermentation. For example, while methods utilizing *Escherichia coli* (*E. coli*) K-12 strain have been reported in Japanese Patent Laid-open (Kokai) No. 56-35992 and literature (Chattapadhyay, M. K. et al., *Med. Sci. Res.* 23, 775 (1995); Chattapadhyay, M. K. et al., *Biotechnol. Lett.* 17, 567-570 (1995)), any of these methods cannot provide L-methionine production amount sufficient for industrial use.

In *E. coli*, the biosynthetic pathway of L-methionine is partly shared with the biosynthetic pathway of L-threonine, and L-homoserine serves as a common intermediate. The first step of the peculiar pathway from L-homoserine to L-methionine is catalyzed by homoserine transsuccinylase (HTS). This enzyme has been known to suffer concerted inhibition by the final product, L-methionine, and a metabolite of L-methionine, S-adenosylmethionine (Lee, L.-W. et al., *J. Biol. Chem.*, 241, 5479-5480 (1966)).

The nucleotide sequence of the metA gene encoding homoserine transsuccinylase of *E. coli*, has been reported by Duclos et al. (Duclos, B. et al., *Nucleic Acids Res.* 17, 2856 (1989)), and a method for obtaining a strain having a mutation for metA using resistance to an analog of L-methionine, α-methyl-DL-methionine (MM) has also been known (Chattopadhyay, M. K. et al., *J. Gen. Microbiol.*, 137, 685-691 (1991)). It has been reported for *Salmonella typhimurium* that, the metA gene product, homoserine transsuccinylase, was an inhibition-desensitized type as for the inhibition by L-methionine and S-adenosylmethionine synthase (SAM) in an MM resistant strain (Lawrence, D. A. et al., *J. Bacteriol.*, 109, 8-11 (1972)). However, the nucleotide sequence of the mutant meta gene has not been reported. Furthermore, it has been reported that a mutant having a sole mutation in metA did not secret L-methionine (Chattopadhyay, M. K. et al., *J. Gen. Microbiol.*, 137, 685-691 (1991)).

It has also been revealed that the expression of the genes including metA of the enzymes for the reaction by homoserine transsuccinylase and subsequent reactions in the peculiar biosynthetic pathway of L-methionine suffers inhibition by a repressor which is a metJ gene product (Green, R. C. Biosynthesis of Methionine in "*Escherichia coli* and *Salmonella* Cellular and Molecular Biology/Second Edition", ed. Neidhardt, F. D., ASM Press, pp. 542-560 (1996)). It has also been known that the metJ gene is adjacent to the metBL operon in a reverse direction, which operon consists of the metB gene coding for the second enzyme of the peculiar biosynthetic pathway for L-methionine, cystathionine γ-synthase, and metL coding for aspartokinase-homoserine dehydrogenase II (AK-HDII) (Duchange, N. et al., *J. Biol. Chem.*, 258, 14868-14871 (1983)).

It has been suggested that metK coding for S-adenosylmethionine, which catalyzes the metabolic reaction from L-methionine to S-adenosylmethionine, should be an essential enzyme (Green, R. C. Biosynthesis of Methionine in "*Escherichia coli* and *Salmonella* Cellular and Molecular Biology/Second Edition", ed. Neidhardt, F. D., ASM Press, pp. 542-560 (1996)). Furthermore, it has also been known that a metK mutant strain can be obtained based on resistance to a methionine analogue such as DL-norleucine and ethionine (Chattopadhyay, M. K. et al., *J. Gen. Microbiol.*, 137, 685-691 (1991)), and can increase the expression of the enzymes of the peculiar biosynthetic pathway of L-methionine (Greene, R. C. et al., *J. Bacteriol.*, 115, 57-67).

As mentioned above, there have been reported enzymes involved in the L-methionine biosynthesis and genes therefor to some extent. However, only few findings that directly lead to the production of L-methionine by fermentation have been obtained, and hence hardly applied to breeding of L-methionine-producing bacteria.

SUMMARY OF THE INVENTION

The present invention has been accomplished in view of the aforementioned current technical status, and an object of the present invention is to elucidate factors affecting the L-methionine production, thereby breeding L-methionine-producing bacteria, and enabling L-methionine production by fermentation.

In order to achieve the aforementioned object, the present inventors earnestly conducted studies, and as a result, accomplished the present invention.

That is, the present invention provides:

(1) A microorganism which is deficient in repressor of L-methionine biosynthesis system and has L-methionine productivity;

(2) a microorganism having enhanced intracellular homoserine transsuccinylase activity and L-methionine productivity;

(3) a microorganism which is deficient in repressor of L-methionine biosynthesis system, and has enhanced intracellular homoserine transsuccinylase activity and L-methionine productivity;

(4) the microorganism according to any one of the above (1)-(3), which further exhibits reduced intracellular S-adenosylmethionine synthetase activity;

(5) the microorganism according to any one of the above (2)-(4), wherein the enhanced intracellular homoserine transsuccinylase activity is obtained by increasing copy number of a gene encoding homoserine transsuccinylase, or enhancing an expression regulatory sequence for the gene;

(6) the microorganism according to the above (1) or (4), which has homoserine transsuccinylase for which concerted inhibition by L-methionine and S-adenosylmethionine is desensitized;

(7) the microorganism according to any one of the above (1)-(6), which exhibits L-threonine auxotrophy;

(8) the microorganism according to any one of the above (1)-(7), which exhibits enhanced intracellular cystathionine γ-synthase activity and enhanced intracellular aspartokinase-homoserine dehydrogenase II activity;

(9) the microorganism according to any one of the above (1)-(8), which belongs to the genus *Escherichia*;

(10) a method for producing L-methionine which comprises culturing the microorganism according to any one of the above (1)-(9) in a medium to produce and accumulate L-methionine in the medium, and collecting the L-methionine from the medium; and

(11) A DNA which codes for homoserine transsuccinylase for which concerted inhibition by L-methionine and S-adenosylmethionine is desensitized, wherein the homoserine transsuccinylase has the amino acid sequence of SEQ ID NO: 26 including a mutation corresponding to replacement of arginine by cysteine at the 27th position, mutation corresponding to replacement of isoleucine by serine at the 296th position, mutation corresponding to replacement of proline by leucine at the 298th position, mutation corresponding to replacement of arginine by cysteine at the 27th position and replacement of isoleucine by serine at the 296th position, mutation corresponding to replacement of isoleucine by serine at the 296th position and replacement of proline by leucine at the 298th position, mutation corresponding to replacement of proline by leucine at the 298th position and replacement of arginine by cysteine at the 27th position, or mutation corresponding to replacement of arginine by cysteine at the 27th position, replacement of isoleucine by serine at the 296th position and replacement of proline by leucine at the 298th position.

In this specification, S-adenosylmethionine will occasionally be abbreviated as "SAM", α-methyl-DL-methionine as "MM", and DL-norleucine as "NL". Further, S-adenosylmethionine synthetase will be occasionally be abbreviated as "SAM synthetase", and homoserine transsuccinylase as "HTS". The metB gene product, cystathionine γ-synthase, of *E. coli* may also be called as "cystathionine synthase", and the metL gene product, "aspartokinase homoserine dehydrogenase II", may also be called as AK-HDII.

The term "L-methionine productivity" used for the present invention means an ability to accumulate L-methionine in a medium when a microorganism is cultured in the medium.

According to the present invention, there is provided a microorganism having L-methionine production ability. The microorganism can be utilized as an L-methionine-producing bacterium or a material for breeding of L-methionine-producing bacteria.

The mutant metA gene of the present invention can be utilized for the breeding of L-methionine-producing bacteria, because the concerted inhibition by L-methionine and SAM for the enzyme encoded by it is canceled.

DETAILED DESCRIPTION OF THE INVENTION

Hereafter, the present invention will be explained in detail.

The microorganism of the present invention is a microorganism which is deficient in repressor of the L-methionine biosynthesis system and has L-methionine productivity, or a microorganism which has enhanced intracellular homoserine transsuccinylase activity and L-methionine productivity. The microorganism of the present invention is preferably a microorganism which is deficient in repressor of the L-methionine biosynthesis system, and has enhanced intracellular homoserine transsuccinylase activity. The microorganism of the present invention further preferably exhibits reduced intracellular SAM synthetase activity.

The aforementioned microorganism of the present invention is not particularly limited, so long as it has a pathway for producing L-methionine and SAM from L-homoserine via O-acylhomoserine which is produced from L-homoserine by the acyl-transferring reaction, and its expression of the acyl transferase is controlled through suppression by a repressor. While such a microorganism may be an *Escherichia* bacterium, *coryneform* bacterium, and *Bacillus* bacterium, it is preferably an *Escherichia* bacterium, for example, *E. coli*.

If the microorganism of the present invention is a bacterium in which HTS possessed by the microorganism suffers concerted inhibition by SAM and L-methionine like *E. coli*, its L-methionine productivity may be improved by canceling the inhibition.

As the peculiar pathway for the methionine biosynthesis, there are one which uses cystathionine as an intermediate as in many microorganisms such as *E. coli*, and one which does not use cystathionine as in *Brevibacterium flavum* (Ozaki, H. et al., *J. Biochem.*, 91, 1163 (1982)). In the present invention, a microorganism that uses cystathionine is preferred. In such a microorganism, L-methionine productivity can be increased by enhancing the intracellular cystathionine synthase activity. In addition, even if it is a microorganism like *Brevibacterium flavum*, L-methionine productivity may be enhanced by deficiency of repressor in the L-methionine biosynthesis system and/or enhancement of HTS.

Furthermore, in the aforementioned microorganism, L-methionine productivity can further be increased by enhancing at least one of the aspartokinase activity and the homoserine dehydrogenase activity, which are involved in the shared pathway of the L-methionine biosynthesis and the L-threonine biosynthesis.

When two or more of the aforementioned characteristics are imparted to a microorganism, the order for imparting them is not particularly limited, and they can be given in an arbitrary order. Moreover, when multiple genes are introduced into a microorganism, those genes may be carried by the same vector, or may be separately carried by multiple different vectors. When multiple vectors are used, it is preferred to use vectors having different drug markers and different replication origins.

Methods for imparting each of the aforementioned characteristics to a microorganism will be explained below.

<1> Deficiency of Repressor in L-Methionine Biosynthesis System

A microorganism deficient in a repressor in the L-methionine biosynthesis system can be obtained by subjecting microorganisms to a mutagenic treatment, and selecting a strain no longer producing the repressor. The mutagenic treatment can be performed with means usually used for obtaining microbial mutants, for example, UV irradiation or treatment with an agent used for mutagenesis such as N-methyl-N'-nitrosoguanidine (NTG) and nitrous acid.

The repressor can also be made deficient by destroying a gene coding for the repressor on chromosomal DNA of the microorganism. The gene can be destroyed by preparing a deleted type gene which has deletion of at least a part of a coding region or expression regulatory sequence, and causing homologous recombination of the deleted type gene and a gene on the chromosome to substitute the deleted type gene for the gene on the chromosome (gene substitution).

Since the nucleotide sequence of the gene coding for the repressor in the L-methionine biosynthesis system of *E. coli* (metJ) has been known (Duchange, N. et al., *J. Biol. Chem.*, 258, 14868-14871 (1983)), the repressor can be isolated from chromosomal DNA, for example, by PCR using primers produced based on the nucleotide sequence. A deleted type gene can be obtained by excising a certain region from the gene fragment obtained as described above, and deleting at least a part of the coding region or expression regulatory region.

The gene substitution can be performed, for example, as follows. A deleted type gene is introduced into a vector having a temperature sensitive replication origin to prepare a recombinant vector, and a microorganism is transformed with the recombinant vector so that the deleted type gene should be inserted into a gene on chromosomal DNA by homologous recombination of the deleted type gene and the gene on the chromosomal DNA. Then, the transformant strain is cultured at a temperature at which the vector cannot replicate to drop out the vector from cytoplasm. Furthermore, the gene is replaced when one copy of the gene on the chromosome is dropped out with the vector. The occurrence of the desired gene substitution can be confirmed by Southern hybridization analysis of the chromosomal DNA of a strain to be to be tested for the gene substitution.

As a vector for *E. coli* that has a temperature sensitivity replication origin, for example, the plasmid pMAN997 disclosed in Japanese Patent Application No. 9-194603 and the like can be mentioned. As a vector for coryneform bacteria that has a temperature sensitivity replication origin, for example, the plasmid pHSC4 disclosed in Japanese Patent Laid-open No. 5-7491 and the like can be mentioned. However, the vector is not limited to these, and other vectors can also be used.

As mentioned above, it has known for *E. coli* that the metJ gene is adjacent to the metBL operon, which consists of metB gene and metL gene, in the reverse direction (Duchange, N. et al., *J. Biol. Chem.*, 258, 14868-14871 (1983)). Therefore, if a suitable promoter sequence is ligated to a deleted type metJ gene and gene substitution is performed as described above, the destruction of the metJ gene and improvement of expression utilizing substitution of promoter in the metBL operon can simultaneously be obtained by one homologous recombination. Improved expression of the metBL operon enhances the intracellular cystathionine synthase activity and AK-HDII activity.

Specifically, the following three components, a fragment of about 1 kb containing the metB gene, which is obtained by, for example, PCR (polymerase chain reaction; White, T. J. et al.; *Trends Genet.*, 5, 185 (1989)) utilizing chromosomal DNA of *E. coli* W3110 at strain as a template, and oligonucleotides having the nucleotide sequences of SEQ ID NO: 5 and SEQ ID NO: 6 as primers; a fragment of about 1 kb containing the downstream region of the metJ gene obtained by PCR utilizing oligonucleotides having the nucleotide sequences of SEQ ID NO: 7 and SEQ ID NO: 8 as primers; and a sequence having a promoter sequence of the threonine operon, which is obtained by annealing of the oligonucleotides represented as SEQ ID NO: 9 and SEQ ID NO: 10, can be inserted into a suitable vector, and ligating to it to obtain a recombinant vector which contains a DNA fragment having deletion of the structural gene of metJ and substitution of threonine promoter for the promoter of the metBL operon.

To introduce the recombinant DNA prepared as described above to bacterium, any known transformation methods can be employed. For instance, employable are a method of treating recipient cells with calcium chloride so as to increase the permeability of DNA, which has been reported for *Escherichia coli* K-12 [see Mandel, M. and Higa, A., *J. Mol. Biol.*, 53, 159 (1970)]; and a method of preparing competent cells from cells which are at the growth phase followed by introducing the DNA thereinto, which has been reported for *Bacillus subtilis* [see Duncan, C. H., Wilson, G. A. and Young, F. E., *Gene*, 1, 153 (1977)]. Alternatively, it is also possible to apply a method in which DNA recipient cells are allowed to be in a state of protoplasts or spheroplasts capable of incorporating recombinant DNA with ease to introduce recombinant DNA into the DNA recipient cells, as known for *Bacillus subtilis*, actinomycetes, and yeasts (Chang, S, and Choen, S, N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Acad. Sci. USA*, 75, 1929 (1978)). Transformation of coryneform bacteria may performed by the electric pulse method (refer to Japanese Patent Publication Laid-Open No. 2-207791).

The vector to be used for cloning the genes such as metA, metK and thrBC as described below includes, for example, pUC19, pUC18, pBR322, pHSG299, pHSG399, pHSG398, RSF1010 and the like. Besides, it is possible to use phage DNA vectors. When microorganisms other than *E. coli* are used, it is preferable to use a shuttle vector autonomously replicable in those microorganisms and *E. coli*. As examples of plasmid autonomously replicable in coryneform bacteria, for example, the followings can be mentioned.

pAM330 (see Japanese Patent Laid-open No. 58-67699)
pHM1519 (see Japanese Patent Laid-open No. 58-77895)
pAJ655 (see Japanese Patent Laid-open No. 58-192900)
pAJ611 (see the same)
pAJ1844 (see the same)
pCG1 (see Japanese Patent Laid-open No. 57-134500)
pCG2 (see Japanese Patent Laid-open No. 58-35197)
pCG4 (see Japanese Patent Laid-open No. 57-183799)
pCG11 (see the same)
pHK4 (see Japanese Patent Laid-open No. 5-7491)

In order to prepare recombinant DNA by ligating the gene fragment and a vector, the vector is digested by restriction enzyme(s) corresponding to the termini of the gene fragment. Ligation is generally performed by using a ligase such as T4 DNA ligase.

The methods to perform, for example, preparation of the genomic DNA library, hybridization, PCR, preparation of plasmid DNA, digestion and ligation of DNA, and design of oligonucleotide used for primers are described by Sambrook, J., Fritsche, E. F., Maniatis, T. in Molecular Cloning, Cold Spring Harbor Laboratory Press (1989).

<2> Enhancement of HTS Activity and Introduction of Mutant HTS

The HTS activity in a microbial cell can be attained by preparing a recombinant DNA through ligation of a gene fragment encoding HTS with a vector which functions in the microorganism, preferably a multi-copy type vector, and transforming the microorganism through introduction of the plasmid into in the microbial cell. As a result of increase of the copy number of the gene encoding HTS in the transformant strain, the HTS activity is enhanced. In *E. coli*, HTS is encoded by the metA gene. When an *Escherichia* bacterium is used as the microorganism, the HTS gene to be introduced is preferably a gene derived from an *Escherichia* bacterium. However, genes derived from other microorganisms having homoserine transacetylase, such as coryneform bacteria, can also be used.

Enhancement of HTS activity can also be achieved by introducing multiple copies of the HTS gene into the chromosomal DNA of the above-described host strains. In order to introduce multiple copies of the HTS gene in the chromosomal DNA of bacterium belonging to the genus *Corynebacterium*, the homologous recombination is carried out using a sequence whose multiple copies exist in the chromosomal DNA as targets. As sequences whose multiple copies exist in the chromosomal DNA, repetitive DNA, inverted repeats exist at the end of a transposable element can be used. Also, as disclosed in Japanese Patent Laid-open No. 2-109985, it is possible to incorporate the HTS gene into transposon, and allow it to be transferred to introduce multiple copies of the HTS gene into the chromosomal DNA. By either method, the number of copies of the HTS gene within cells of the transformant strain increases, and as a result, HTS activity is enhanced.

The enhancement of HTS activity can also be obtained by, besides being based on the aforementioned gene enhancement, enhancing an expression regulatory sequence for the HTS gene. Specifically, it can be attained by replacing an expression regulatory sequence of HTS gene on chromosome DNA or plasmid, such as a promoter, with a stronger one (see Japanese Patent Laid-open No. 1-215280). For example, lac promoter, trc promoter, tac promoter, PR promoter and PL promoter of lambda phage and the like are known as strong promoters. Substitution of these promoters enhances expression of the HTS gene, and hence the HTS activity is enhanced.

Since the nucleotide sequence of the HTS gene (metA) of E. coli has been known (Blattner, F. R. et al., *Science,* 277, 1453-1462 (1997)), it can be isolated from chromosomal DNA by PCR using primers produced based on the nucleotide sequence. As such primers, the oligonucleotides having the nucleotide sequences represented as SEQ ID NO: 21 and SEQ ID NO: 22 are specifically mentioned.

It is expected that, by enhancing the HTS activity in a microbial cell as described above, L-methionine biosynthesis can be enhanced, and thus the L-methionine production amount can be increased.

Further, because HTS suffers concerted inhibition by L-methionine and SAM, the L-methionine biosynthesis system can also be enhanced by obtaining a microorganism containing HTS for which concerted inhibition has been canceled. Such a microorganism containing HTS for which concerted inhibition has been canceled can be obtained by subjecting microorganisms to a mutagenic treatment, and selecting a strain containing HTS for which concerted inhibition has been canceled. The mutagenic treatment can be performed with means usually used for obtaining microbial mutants, for example, UV irradiation or treatment with an agent used for mutagenesis such as N-methyl-N'-nitrosoguanidine (NTG) and nitrous acid. The expression "HTS for which concerted inhibition has been canceled" herein used means HTS exhibiting a ratio of its enzymatic activity in the presence of L-methionine, SAM or L-methionine and SAM to its enzymatic activity in the absence of L-methionine and SAM (remaining ratio) higher than that of a wild-type HTS. Specifically, an HTS exhibiting a remaining ratio in the presence of 1 mM L-methionine of 40% or more, preferably 80% or more, a remaining ratio in the presence of 1 mM SAM of 10% or more, preferably 50% or more, or a remaining ratio in the presence of 0.1 mM each of L-methionine and SAM of 15% or more, preferably 60% or more is an HTS for which concerted inhibition by L-methionine and SAM has been canceled.

A mutant strain having such a mutant HTS as mentioned above can be obtained by culturing a parent strain in the presence of α-methyl-DL-methionine (MM), e.g., in a medium containing 1 g/l of MM, and selecting a strain growing on the medium. The selection with MM may be repeated two or more times.

A mutant strain having a mutant HTS can also be obtained by cloning the mutant HTS gene (mutant metA) from a HTS mutant obtained as described above, and transforming a microorganism with the mutant gene. Isolation of a mutant HTS gene and introduction of the gene into a microorganism can be performed as the aforementioned wild-type HTS gene. As HTS having a mutant metA gene, HTS having the amino acid sequence of SEQ ID NO: 26 including a mutation corresponding to replacement of arginine by cysteine at the 27th position, mutation corresponding to replacement of isoleucine by serine at the 296th position, or mutation corresponding to replacement of proline by leucine at the 298th position can specifically be mentioned. HTS including two or more of these mutations is also a preferred mutant HTS.

<3> Attenuation of SAM Synthetase Activity

Furthermore, the L-methionine productivity of microorganism can be increased by attenuating intracellular SAM synthetase activity. The L-methionine productivity of a microorganism can also be increased by making the microorganism SAM synthetase activity deficient, but in such a case, the medium for culturing the microorganism must contain SAM. Therefore, it is preferable to attenuate SAM synthetase activity. The expression "attenuating SAM synthetase activity" herein used means that a specific activity of SAM synthetase per unit of protein in microbial cells is made lower than that of a strain having a wild-type SAM synthetase. Specifically, the degree of attenuation, i.e., the reduced activity may be 80% to 50%, preferably 50% to 30%, more preferably 30% to 10% of the SAM synthetase activity of a wild-type strain. In E. coli, it has been suggested that, if the specific activity of SAM synthetase falls below 10%, cell division would be inhibited (Newman, E. B. et al., *J. Bacteriol.,* 180, 3614-3619 (1998)).

The microorganism whose SAM synthetase activity is reduced may be one producing SAM synthetase exhibiting a reduced specific activity per enzymatic protein (reduced type SAM synthetase), or one in which expression efficiency of the enzyme is reduced because of reduced transcription efficiency or reduced translation efficiency of SAM synthetase gene.

A mutant strain whose SAM synthetase activity is reduced may be obtained by culturing a parent strain in the presence of DL-norleucine (NL), e.g., in a medium containing 0.1 g/l of NL, and selecting a grown strain. The selection with NL may be repeated two or more times. It is also possible to use ethionine or γ-glutamylmethyl ester instead of DL-norleucine.

A mutant strain having an reduced type SAM synthetase can also be obtained by cloning a gene for the reduced type SAM synthetase from a SAM synthetase-reduced strain obtained as described above, and substituting the mutant gene for a wild-type SAM synthetase gene on a chromosome of microorganism. The gene substitution of SAM synthetase gene can be performed in the same manner as the aforementioned metJ gene. Since the nucleotide sequence of the SAM synthetase gene (metK) of E. coli has been known (Blattner, F. R. et al., *Science,* 277, 1453-1462 (1997)), it can be isolated from chromosomal DNA by PCR using primers produced based on the nucleotide sequence. As such primers, the oligonucleotides having the nucleotide sequences represented as SEQ ID NO: 11 and SEQ ID NO: 12 are specifically mentioned. The occurrence of the desired mutation in the obtained metK gene can be confirmed by determining the nucleotide sequence of the gene, and comparing it with a known nucleotide sequence of wild-type metK gene.

As specific examples of the gene coding for an reduced type SAM synthetase, those coding for SAM synthetases having the amino acid sequence of SEQ ID NO: 18 including a mutation corresponding to replacement of isoleucine by leucine at the 303rd position, mutation corresponding to replacement of valine by glutamic acid at the 185th position, or mutation corresponding to replacement of arginine at the 378th position and subsequent amino acid residues by a sequence of alanine-methionine-leucine-proline-valine (SEQ ID NO: 29) can be mentioned.

<4> L-Threonine Auxotrophy

L-methionine productivity can be improved by imparting L-threonine auxotrophy to a microorganism. Specific examples of a microorganism exhibiting L-threonine auxotrophy include those having deficiency of any one of enzymes involved in the peculiar pathway of L-threonine biosynthesis from L-homoserine to L-threonine. In *E. coli*, the genes of the enzymes involved in the biosynthesis of L-threonine exist as the threonine operon (thrABC), and L-threonine auxotrophic strain, which has lost the ability to synthesize L-homoserine and subsequent products, can be obtained by deleting the thrBC segment. The thrA gene codes for one of the isozymes of aspartokinase, which is an enzyme of the shared pathway of the L-methionine and L-threonine biosyntheses, and hence it is preferably not to be deleted.

In order to delete thrBC, the thrBC segment in the threonine operon on chromosomal DNA can be destroyed. thrBC can be destroyed by replacing the thrBC segment on a microbial chromosome with thrBC a part of which is deleted. The gene substitution of thrBC may be performed in the same manner as in the gene substitution of the aforementioned metJ gene. A thrBC segment containing deletion can be obtained by amplifying a fragment of about 1 kb containing the upstream region of the thrB gene by PCR using *E. coli* chromosomal DNA as a template and primers having the nucleotide sequences of SEQ ID NOS: 1 and 2, similarly amplifying a fragment of about 1 kb containing the downstream region of the thrC gene by PCR using primers having the nucleotide sequences of SEQ ID NOS: 3 and 4, and ligating these amplified products.

<5> Production of L-Methionine

L-methionine can be produced by culturing a microorganism having L-methionine productivity prepared as described above in a medium so that L-methionine should be produced and accumulated in the medium, and collecting L-methionine from the medium.

The medium to be used may be selected from well-known media conventionally used depending on the kind of microorganism to be used. That is, it may be a usual medium that contains a carbon source, nitrogen source, inorganic ions, and other organic ingredients as required. Any special medium is not needed for the practice of the present invention.

As the carbon source, it is possible to use sugars such as glucose, lactose, galactose, fructose or starch hydrolysate; alcohols such as glycerol or sorbitol; or organic acids such as fumaric acid, citric acid or succinic acid.

As the nitrogen source, it is possible to use inorganic ammonium salts such as ammonium sulfate, ammonium chloride or ammonium phosphate; organic nitrogen such as soybean hydrolysate; ammonia gas; or aqueous ammonia.

It is desirable to allow required substances such as vitamin B1, L-threonine and L-tyrosine or yeast extract to be contained in appropriate amounts as organic trace nutrients. Other than the above, potassium phosphate, magnesium sulfate, iron ion, manganese ion and the like are added in small amounts, if necessary.

Cultivation is preferably carried out under an aerobic condition for 16-120 hours. The cultivation temperature is preferably controlled at 25° C. to 45° C., and pH is preferably controlled at 5-8 during cultivation. Inorganic or organic, acidic or alkaline substances as well as ammonia gas or the like can be used for pH adjustment.

Any special techniques are not required for collecting L-methionine from the medium after the cultivation in the present invention. That is, the present invention can be practiced by a combination of well-known techniques such as techniques utilizing ion exchange resin and precipitation.

BEST MODE FOR CARRYING OUT THE INVENTION

The present invention will further be explained more specifically with reference to the following examples.

Example 1

Acquisition of L-Threonine Auxotrophic Strain and metJ Deficient Strain from *Escherichia coli* W3110 Strain <1> Preparation of Plasmid for Recombination Containing thrBC Structural Gene Having Deletion Chromosomal DNA was prepared from W3110 strain, which was a derivative of the wild-type K-12 strain of *E. coli*, by using a genomic DNA purification kit (Advanced Genetic Technology) according to the instruction of the kit. Oligonucleotides having the nucleotide sequences of SEQ ID NO: 1 and SEQ ID NO: 2 in Sequence Listing were synthesized. PCR was performed according to the method of Erlich et al. (PCR Technology-Principles and Applications for DNA Amplification, ed. Erlich, H. A., Stockton Press) by using the above oligonucleotides as primers and the aforementioned chromosomal DNA as the template to amplify a fragment of about 1 kb containing the upstream region of the thrB gene. This amplification fragment was introduced with recognition sequences for EcoRI and SalI, which were derived from the primers. The obtained amplified fragment was digested with restriction enzymes corresponding to the introduced recognition sites.

Similarly, PCR was performed by using oligonucleotides having the nucleotide sequences of SEQ ID NO: 3 and SEQ ID NO: 4 as primers to amplify a fragment of about 1 kb containing the downstream region of the thrC gene. This amplification fragment was introduced with recognition sequences for SalI and HindIII, which were derived from the primers. The obtained amplified fragment was digested with restriction enzymes corresponding to the introduced recognition sites. The aforementioned two amplified fragments, and pHSG398 (TAKARA SHUZO) digested with EcoRI and HindIII were ligated by using a ligation kit (TAKARA SHUZO), and *E. coli* JM109 competent cells (TAKARA SHUZO) were transformed with the ligation product. Plasmids were prepared from the transformants based on the alkaline method (Boirnboim, H. C. et al., *Nucleic Acids Res.*, 7, 1513-1523 (1979)) by using a Plasmid Extractor PI-50 (Kurabo Industries, Ltd.). From the obtained plasmids, a plasmid in which two fragments were inserted in the EcoRI and HindIII recognition sites through SalI recognition sites was selected based on the lengths of inserted fragments. This plasmid contained the upstream and the downstream regions of the structural gene of thrBC, and contained a gene fragment in which substantially full length of the structural gene of thrBC was deleted.

<2> Production of thrBC Structural Gene Deletion Strain by Genetic Recombination The aforementioned plasmid and the plasmid pMAN997 having a temperature sensitive replication origin, which was disclosed in Japanese Patent Application No. 9-194603, were digested with EcoRI and HindIII, and ligated each other. The *E. coli* JM109 strain was transformed with the obtained recombinant plasmid. Plasmids were extracted from the transformants, and one having a structure where a thrBC-deleted gene fragment was inserted in pMAN997 was selected, and designated as pMANΔBC. The W3110 strain was transformed with this plasmid to perform genetic recombination in a conventional manner. That is, selection of recombinant strains was carried out based on the L-threonine auxotrophy in M9 medium (Sambrook, J. et al., "Molecular Cloning: A Laboratory Manual/Second Edition", Cold Spring Harbor Laboratory Press, A.3 (1989)), and the obtained L-threonine auxotrophic strain was designated as WΔBC strain.

<3> Production of metJ Deficient Strains from W3110 Strain and WΔBC Strain

Then, PCR was performed by using the W3110 strain chromosomal DNA as the template and oligonucleotides having the nucleotide sequences of SEQ ID NO: 5 and SEQ ID NO: 6 as primers to amplify a fragment of about 1 kb containing the metB gene. This amplification fragment was introduced with recognition sequences for EcoRI and SphI. The obtained amplified fragment was digested with restriction enzymes corresponding to the introduced recognition sites.

Similarly, PCR was performed by using oligonucleotides having the nucleotide sequences of SEQ ID NO: 7 and SEQ ID NO: 8 as primers to amplify a fragment of about 1 kb containing the downstream region of the metJ gene. This amplification fragment was introduced with recognition sequences for SalI and HindIII. The obtained amplified fragment was digested with restriction enzymes corresponding to the introduced recognition sites.

Then, a sequence represented as SEQ ID NO: 9, which contained SphI and HindIII recognition sites at the both ends and the promoter sequence of the threonine operon, and its complementary strand represented as SEQ ID NO: 10 were synthesized, annealed, and digested with restriction enzymes SphI and HindIII. The threonine promoter fragment obtained as described above, pHSG298 (TAKARA SHUZO) digested with EcoRI, and the aforementioned two PCR amplification fragments were mixed, and ligated. The JM109 strain was transformed with this ligation solution, and plasmids were extracted from the transformants. A plasmid comprising ligated four of the components was selected from the obtained plasmids. This plasmid had a structure where the metJ structural gene was deleted, and the promoter of metBL operon was replaced with the threonine promoter.

The plasmid obtained above and the plasmid pMAN997 having a temperature sensitive replication origin, which is disclosed in Japanese Patent Application No. 9-194603, were digested with EcoRI, and ligated each other. A plasmid having a structure where a metJ-deleted fragment was inserted into pMAN997 was selected, and designated as pMANΔJ. The W3110 strain and the WΔBC strain were transformed with this plasmid to perform genetic recombination in a conventional manner. Selection of recombinant strains was performed based on the lengths of amplified products from PCR utilizing DNA prepared from the cells as the template, and the oligonucleotides represented in SEQ ID NO: 6 and SEQ ID NO: 8 as primers. The metJ-deleted strains obtained from the W3110 strain and the WΔBC strain were designated as WΔJ strain and WΔBCΔJ strain, respectively.

In order to confirm the effect of the metJ deletion by the recombination, a crude enzyme extract was prepared from the cells, and the activities of HTS and cystathionine synthase were measured. The W3110 strain and the WΔJ strain were each inoculated to 2 ml of LB medium, and cultured at 37° C. overnight. 1 ml of the medium was centrifuged at 5,000 rpm for 10 minutes, and the cells were washed twice with 0.9% saline. The obtained cell were suspended in 1 ml of 0.9% saline, 0.5 ml of which was inoculated to 50 ml of Davis-Mingioli minimal medium (Davis B. D., and Mingioli, E. S., J. Bacteriol., 60, 17-28 (1950)) containing 5 mM L-methionine. The cells were cultured at 37° C. for 24 hours, then the medium was centrifuged at 8,000 rpm for 10 minutes, and the cells were washed twice with 0.9% saline. The cells were suspended in 3 ml of 50 mM potassium phosphate buffer (pH 7.5) containing 1 mM dithiothreitol. This suspension was subjected to a cell disruption treatment at 4° C. with a power of 150 W for 5 minutes by using an ultrasonicator (Kubota Co.). The sonicated suspension was centrifuged at 15,000 rpm for 30 minutes, and the supernatant was desalted in a Sephadex G-50 column (Pharmacia) to obtain a crude enzyme extract. The HTS activity and the cystathionine synthase activity in the crude enzyme extract were measured.

As for the HTS activity, 5 µl of the crude enzyme extract was added to a reaction mixture comprising 0.1 M potassium phosphate (pH 7.5), 1 mM succinyl-coenzyme A (Sigma), 0.2 nM DL-[$^{14}$C]homoserine (Muromachi Chemical Industry), and 0.2 mM L-homoserine to obtain a volume of 50 µl, and allowed to react at 30° C. for 10 minutes. 1 µl of the reaction mixture was spotted on a cellulose plate (Merck), and developed with a mixed solvent containing acetone, butanol, water, and diethylamine at a ratio of 10:10:5:2. After the plate was air-dried, autoradiography was performed by using an image analyzer (Fuji Photo Film).

The cystathionine synthase has been known to produce α-ketobutyric acid, ammonia, and succinic acid from O-succinylhomoserine in the absence of L-cysteine, and this can be utilized for simple detection thereof (Holbrook, E. L. et al., Biochemistry, 29, 435-442 (1990)). 100 µl of the crude enzyme extract was added to a reaction mixture comprising 0.2 M Tris-HCl (pH 8), mM O-succinylhomoserine (Sigma), and 0.25 mM pyridoxal phosphate (Sigma) to obtain a volume of 1 ml, allowed to react at 37° C. for 20 minutes, and cooled with ice. The O-succinylhomoserine in this reaction mixture was quantitated by reverse phase HPLC (GL Sciences), and the reduced amount of O-succinylhomoserines was calculated by using a reaction mixture not added the crude enzyme extract. The reaction was also performed with no addition of pyridoxal phosphate, and pyridoxal phosphate-dependent reduction of O-succinylhomoserine was defined to be the cystathionine synthase activity.

The specific activities for the HTS activity and the cystathionine synthase activity measured as described above were shown in Table 1. While the HTS activity was hardly detected in the W3110 strain due to the effect of L-methionine addition, marked activity was observed in the WΔJ strain. As also for the cystathionine synthase activity, remarkable increase was observed in the WΔJ strain compared with the W3110 strain. From these results, the effects of the metJ deletion and the promoter substitution in the metBL operon by recombination were confirmed.

TABLE 1

HTS activity and cystathionine synthase activity in metJ deficient strain

| Strain | HTS activity (mmol/min/mg protein) | Cystathionine synthase activity (mmol/min/mg protein) |
|---|---|---|
| W3110 | 0.3 | 140 |
| WΔJ | 126 | 1300 |

Example 2

Acquisition of metK Mutant from W3110 Strain

The W3110 strain was cultured in LB medium (Sambrook, J. et al., "Molecular Cloning: A Laboratory Manual/Second Edition", Cold Spring Harbor Laboratory Press, A.1 (1989)) at 37° C. overnight. 1 ml of the cultured medium was centrifuged at 5,000 rpm for 10 minutes, and the cells were washed twice with 0.9% saline. The obtained cells were suspended in 100 µl of 0.9% saline, 10 µl of which was inoculated to 5 ml of Davis-Mingioli minimal medium containing 0.1 g/l of DL-norleucine (NL), and cultured at 37° C. for 5 days.

Some of the grown colonies were subjected to colony separation on LB agar medium, and their growth was confirmed again in Davis-Mingioli minimal medium containing 0.1 g/l of NL to select 12 NL-resistant strains. Chromosomal DNA was prepared from these resistant strains. PCR was performed by using this chromosomal DNA as a template and two sorts of primers having the sequences of SEQ ID NOS: 11 and 12 to amplify the metK gene. The nucleotide sequence of this amplification fragment was determined by using amplification primers of which sequences are shown as SEQ ID NO: 11 and 12, and primers of which sequences are shown as SEQ ID NOS: 13, 14, 15, and 16. The nucleotide sequence determination was performed by using a Dye Terminator Cycle Sequencing Kit (Perkin-Elmer) on a DNA sequencer Model 373S (Perkin-Elmer) in accordance with the instructions attached to them. The nucleotide sequence of the wild strain W3110 determined as a control completely coincided with the sequence of metK reported by Blattner et al. (Blattner, F. R. et al., Science, 277, 1453-1462 (1997)). This sequence is represented as SEQ ID NO: 17. Further, the amino acid sequence of SAM synthetase which may be encoded by the sequence of SEQ ID NO: 17 is shown in SEQ ID NO: 18.

Among the NL resistant strains, a mutation in the structural gene of metK was found in 3 strains out of the 12 strains, which were designated as WNL2, WNL24, and WNL32. As for the metK nucleotide sequences of these mutant strains, in the wild-type nucleotide sequence shown as SEQ ID NO: 17, the WNL2 strain had replacement of adenine by cytosine at the 907th position, the WNL24 strain had replacement of thymine by adenine at the 554th position, and the WNL32 strain had deletion of cytosine at the 1132nd position. As a result, it was found that, in the amino acid sequence of SAM synthetase represented as SEQ ID NO: 18, the SAM synthetase of the WNL2 strain had replacement of isoleucine by leucine at the 303rd position, that of the WNL24 strain had replacement of valine by glutamic acid at the 185th position, and that of the WNL32 strain had replacement of arginine at the 378th position and subsequent amino acid residues by alanine-methionine-leucine-proline-valine due to deletion of one nucleotide. It was estimated that the SAM synthetase activity was reduced in these strains.

Example 3

Production of L-Methionine by Introduction of metK Mutation and Amplification of Wild-Type metA Gene (1) Introduction of metK Mutation into WΔBCΔJ Strain PCR was performed by using each chromosomal DNA of the metK gene mutant strains, WNL2 strain, WNL24 strain, and WNL32 strain, as a template, and oligonucleotides of SEQ ID NO: 19 and SEQ ID NO: 20 as primers to amplify a fragment of about 2.5 kb containing the metK gene. This amplification fragment was introduced with recognition sequences for HindIII at the both ends. The obtained amplified fragment was digested with HindIII. pSTV28 (TAKARA SHUZO) digested with HindIII and the PCR amplification fragment were mixed and ligated, and the JM109 strain was transformed with the ligation product. Plasmids were extracted from the transformants. From the obtained plasmids, plasmids inserted with the PCR amplification fragment were selected. As for these plasmids, mutations in the metK structural gene were confirmed by determining their nucleotide sequences.

HindIII digestion fragments of these plasmids were each cloned into pMAN997 digested with HindIII, and the resulting plasmids were designated as pMANK-2, pMANK-24, and pMANK-32, respectively. The WΔBCΔJ strain was transformed with these plasmids to obtain genetic recombination in a conventional manner. Chromosomal DNA was extracted from the recombinant strains, and used as a template together with oligonucleotides having the nucleotide sequences of SEQ ID NO: 11 and SEQ ID NO: 12 as primers to perform PCR, and the amplification products were examined for nucleotide sequence to select those having mutations. The metK mutant strains obtained from the WΔBCΔJ strain were designated as WΔBCΔJK-2 strain, WΔBCΔJK-24 strain, and WΔBCΔJK-32 strain, respectively.

(2) Amplification of metA Gene

PCR was performed by using W3110 strain chromosomal DNA as a template, and oligonucleotides having the nucleotide sequences of SEQ ID NO: 21 and SEQ ID NO: 22 as primers to amplify a fragment of about 1 kb containing the metA gene. This amplification fragment was introduced with recognition sequences for SphI and SalI at the both ends. The obtained amplified fragment was digested with restriction enzymes corresponding to the introduced recognition sites. The digested product was cloned into pHSG398 digested with SphI and SalI. The nucleotide sequence of the inserted fragment was determined by using amplification primers represented as SEQ ID NOS: 21 and 22, and primers having the sequences of SEQ ID NOS: 23 and 24. The determined nucleotide sequence of metA of the wild strain W3110 completely coincided with the sequence of metA reported by Blattner et al. (Blattner, F. R. et al., Science, 277, 1453-1462 (1997)). This sequence is represented as SEQ ID NO: 25. Further, the amino acid sequence of HTS which may be encoded by the sequence of SEQ ID NO: 25 is shown as SEQ ID NO: 26.

A SphI and SalI digestion product of this plasmid, HindIII and SphI digestion product of the threonine promoter of Example 1, and pMW118 (Nippon Gene) digested with HindIII and SalI were mixed and ligated. The JM109 strain was transformed with this reaction mixture, and plasmids were extracted from the transformants. From the obtained plasmids, a plasmid in which the three components were ligated was selected. This plasmid had a structure where the metA gene was positioned at the downstream from the threonine promoter, by which the metA was expressed. This plasmid was designated as pMWPthmetA-W. The W3110 strain, WΔBC strain, WΔBCΔJ strain, WΔBCΔJK-2 strain, WΔBCΔJK-24 strain, and WΔBCΔJK-32 strain were transformed with this plasmid to obtain transformants.

Each transformant was cultured at 37° C. overnight on an LB plate containing 50 mg/l of ampicillin. The cells were inoculated to 20 ml of medium at pH 7 containing 40 g/l of glucose, 1 g/l of magnesium sulfate, 16 g/l of ammonium sulfate, 1 g/l of potassium dihydrogenphosphate, 2 g/l of yeast extract (Bacto Yeast-Extract, Difco), 0.01 g/l of manganese sulfate, 0.01 g/l of iron sulfate, 30 g/l of calcium carbonate, 50 mg/l of ampicillin, and 0.5 g/l of L-threonine, and cultured at 37° C. for 48 hours.

The cells were separated from the culture, and the amount of L-methionine was measured by an amino acid analyzer (Hitachi). The results are shown in Table 2. L-Methionine, which was not detected for the W3110 strain, was increased in the WΔBC strain and the WΔBCΔJ strain. Concerning the metK mutant strains, while the amount of L-methionine decreased in the WΔBCΔJK-2 strain, a comparable amount was observed in the WΔBCΔJK-32 strain, and the amount was increased in the WΔBCΔJK-24 strain. Thus, the effect on the L-methionine production was observed. The WΔBCΔJK-24 strain harboring the plasmid pMWPthrmetA-W was given a private number AJ13425, and it was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on May 14, 1998 as an accession number of FERM P-16808, and transferred from the original deposit to international deposit based on Budapest Treaty on Sep. 27, 1999, and has been deposited as deposition number of FERM BP-6895.

TABLE 2

L-methionine production amount of wild-type metA introduced strains

| Strain | Production amount (g/l) |
|---|---|
| W3110/pMWPthrmetA-W (metA$^e$) | 0.000 |
| WΔBC/pMWPthrmetA-W (thrBC$^-$, metA$^e$) | 0.008 |
| WΔBCΔJ/pMWPthrmetA-W (metBL$^e$, thrBC$^-$, metA$^e$) | 0.022 |
| WΔBCΔJK-2/pMWPthrmetA-W (thrBC$^-$, metJ$^-$, metBL$^e$, metK$^1$, metA$^e$) | 0.014 |
| WΔBCΔJK-24/pMWPthrmetA-W (thrBC$^-$, metJ$^-$, metBL$^e$, metK$^1$, metA$^e$) | 0.141 |
| WΔBCΔJK-32/pMWPthrmetA-W (thrBC$^-$, metJ$^-$, metBL$^e$, metK$^1$, metA$^e$) | 0.023 | metK$^1$: reduced metK,
metA$^e$: enhanced metA,
metBL$^e$: enhanced metBL

Example 4

Acquisition of metA Mutant Strain and Inhibition-Desensitized Type metA Gene

The W3110 strain was inoculated to 2 ml of LB medium, and cultured at 37° C. for 8 hours. 1 ml of the medium was centrifuged at 5,000 rpm for 10 minutes, and the cells were washed twice with 0.9% saline. The obtained cells were suspended in 100 μl of 0.9% saline, 5 μl of which was inoculated to 5 ml of Davis-Mingioli minimal medium containing 1 g/l of α-methyl-DL-methionine (MM), and cultured at 37° C. for 3 days. The medium was properly diluted, plated on Davis-Mingioli minimal medium containing 1 g/l of MM, and cultured at 37° C. overnight. Some of grown colonies were subjected to colony separation on LB agar medium, and their growth was confirmed again on Davis-Mingioli minimal medium containing 1 g/l of MM. This procedure was independently performed 9 times, and six independent resistant strains, each designated as WMM4, WMM5, WMM6, WMM7, WMM8, and WMM9, were obtained.

Chromosomal DNA was prepared from these resistant strains. PCR was performed by using each chromosomal DNA as a template and primers having the sequences represented as SEQ ID NOS: 21 and 22 to amplify the metA gene. The nucleotide sequence of each amplification fragment was determined by using primers for amplification of which nucleotide sequences are represented as SEQ ID NOS: 21 and 22, and primers having the sequences represented as SEQ ID NOS: 23 and 24. As for the metA nucleotide sequence of the resistance strains, in the nucleotide sequence of wild-type metA represented as SEQ ID NO: 25, thymine at the position of 887 was changed to guanine in the WMM4 strain, cytocine at the position of 893 was changed to thymine in the WMM5 strain, was the wild-type sequence was found in the WMM6 strain, a sequence of ATCTC corresponding the 886th to the 890th nucleotides iterated twice, and an insertion sequence consisting of about 1300 nucleotides, called IS2 (Ghosal, D. et al., *Nucleic Acids Res.*, 6, 1111-1122 (1979)), was present between the repeated sequences in the WMM7 and WMM8 strains, and cytosine at the position of 79 was changed to thymine in the WMM9 strain. As a result, it was found that, in the amino acid sequence of HTS represented as SEQ ID NO: 26, the 296th isoleucine was changed to serine in the WMM4 strain, proline at the position of 298 was changed to leucine in the WMM5 strain, proline at the position of 298 and subsequent amino acid residues were changed to a sequence of arginine-leucine-alanine-proline due to an insertion sequence in the WMM7 and WMM8 strains, and arginine at the position of 27 was changed to cysteine in the WMM9 strain.

The strains WMM4, WMM5, WMM9 and WMM7, in which a mutation was observed in the metA structural gene, were each cultured in LB medium contained in a test tube at 37° overnight, and 1 ml of the medium was centrifuged at 5,000 rpm for 10 minutes. The cells were washed twice with 1 ml of 0.9% saline, and suspended in 1 ml of 0.9% saline, 0.5 ml of which was inoculated to 50 ml of minimal medium and cultured at 37° C. for one day. The medium was centrifuged at 8,000 rpm for 10 minutes, and the cells were washed twice with 1 ml of 0.9% saline. The obtained cells were suspended in 3 ml of 50 mM potassium phosphate buffer (pH 7.5) containing 1 mM dithiothreitol, and a crude enzyme extract was obtained in the same manner as in Example 1. The HTS activity in the crude enzyme extract was measured with the reaction composition mentioned in Example 1 in the presence of an inhibitor. The results are shown in Table 3. The activity was undetectable for the WMM7 strain, and this was considered to reflect the marked decrease of the specific activity due to the amino acid sequence change caused by the insertion sequence. The specific activities of the other strains were about ¼ of the wild strain. The inhibition by MM was canceled in all of the WMM4, WMM5, and WMM9 strains, and the inhibition by L-methionine was also reduced considerably. While the inhibition by SAM was hardly canceled in the WMM9 strain, tendency of cancellation was observed in the WMM4 and WMM5 strains. Inhibition by the combination of L-methionine and SAM, which exhibited the strongest inhibition for the wild-type HTS activity, was also markedly reduced in the WMM4 and WMM5 strains

TABLE 3

Activity of HTS derived from MM resistant strains in the presence of various inhibitors

| | HTS activity (mmol/min/mg protein) | | | | |
|---|---|---|---|---|---|
| Inhibitor | W3110 | WMM9 | WMM4 | WMM5 | WMM7 |
| No addition | 22.3 | 5.0 | 4.5 | 4.5 | 0.0 |
| 0.1 mM MM | 18.6 | 4.9 | 4.1 | 4.6 | 0.0 |

TABLE 3-continued

Activity of HTS derived from MM resistant strains in the presence of various inhibitors

| | HTS activity (mmol/min/mg protein) | | | | |
|---|---|---|---|---|---|
| Inhibitor | W3110 | WMM9 | WMM4 | WMM5 | WMM7 |
| 1 mM MM | 7.0 | 2.7 | 4.6 | 4.8 | 0.0 |
| 0.1 mM Met | 14.3 | 2.5 | 4.5 | 4.2 | 0.0 |
| 1 mM Met | 0.8 | 2.2 | 4.0 | 4.0 | 0.0 |
| 0.1 mM SAM | 17.0 | 1.1 | 4.6 | 3.6 | 0.0 |
| 1 mM SAM | 3.0 | 0.5 | 2.6 | 3.3 | 0.0 |
| 0.1 mM SAM + 0.1 mM Met | 0.0 | 0.9 | 5.6 | 2.8 | 0.0 |

Example 5

L-Methionine Production by Introduction of Mutant Meta

PCR was performed by using chromosomal DNA from each of the WMM9, WMM4 and WMM5 strains among the metA mutants obtained in Example 4 as a template, and oligonucleotides having the sequences of SEQ ID NO: 21 and SEQ ID NO: 22 as primers to amplify a fragment containing the metA gene. This amplification fragment had recognition sequences for SphI and SalI at the both ends. The both ends of this amplified fragment were digested with SphI and SalI, and cloned into pHSG398 digested with SphI and SalI. The nucleotide sequence of each insert fragment was determined to confirm the mutation point. A SphI and SalI digestion product of this plasmid, HindIII and SphI digestion product of the threonine promoter mentioned in Example 1, and pMW118 (Nippon Gene) digested with HindIII and SalI were mixed and ligated. The JM109 strain was transformed with this ligation solution, and plasmids were extracted from the transformants. From the obtained plasmids, those comprising ligated three components were selected, and designated as pMWPthrmetA-9, pMWPthrmetA-4, and pMWPthrmetA-5, respectively.

Further, in order to obtain combination of the mutation points of each mutant metA gene, site-specific mutagenesis was performed by using Mutan-Super Express Km (TAKARA SHUZO) according to the instruction of the manufacturer. pMwPthrmetA-9+4 were produced by combining the metA-4 mutation with the metA-9 mutation using an oligonucleotide having the sequence of SEQ ID NO: 27. pMWPthrmetA-9+5 was similarly produced by combining the metA-5 mutation with the metA-9 mutation. Furthermore, pMWPthrmetA-9+4+5 was produced by combining the metA-9 mutation with the metA-4 and metA-5 mutations using an oligonucleotide having the sequence of SEQ ID NO: 28.

The WΔBCΔJK-32 strain was transformed with these plasmids to obtain transformants. Each of the transformants was cultured at 37° C. overnight on an LB plate containing 50 mg/l of ampicillin. The cells were inoculated to 20 ml of medium at pH 7 containing 40 g/l of glucose, 1 g/l of magnesium sulfate, 16 g/l of ammonium sulfate, 1 g/l of potassium dihydrogenphosphate, 2 g/l of yeast extract (Bacto Yeast-Extract, Difco), 0.01 g/l of manganese sulfate, 0.01 g/l of iron sulfate, 30 g/l of calcium carbonate, 50 mg/l of ampicillin, and 0.5 g/l of L-threonine, and cultured at 37° C. for 48 hours. The cells were separated from the culture, and the amount of L-methionine was measured by an amino acid analyzer (Hitachi). The results are shown in Table 4. The amount of L-methionine accumulation increased several times in the strains introduced with a mutant metA, compared with the strain introduced with a wild-type metA. Furthermore, by combining mutations, further increase of L-methionine production amount was obtained.

TABLE 4

L-methionine production amount of mutant metA-introduced strains

| Strain | Amount of L-methionine production (g/l) |
|---|---|
| WΔBCΔΔJK-32/pMWPthrmetA-W | 0.023 |
| WΔBCΔJK-32/pMWPthrmetA-9 | 0.158 |
| WΔBCΔJK-32/pMWPthrmetA-4 | 0.108 |
| WΔBCΔJK-32/pMWPthrmetA-5 | 0.131 |
| WΔBCΔJK-32/pMWPthrmetA-9 + 4 | 0.206 |
| WΔBCΔJK-32/pMWPthrmetA-5 + 9 | 0.207 |
| WΔBCΔJK-32/pMWPthrmetA-9 + 4 + 5 | 0.236 |

What is claimed is:

1. A method for producing L-methionine which comprises culturing a recombinant *Escherichia* bacterium in a medium to produce and accumulate L-methionine in the medium in an amount in excess of the corresponding unmodified *Escherichia* bacterium, and collecting the L-methionine from the medium, wherein the bacterium is deficient in repressor of L-methionine biosynthesis system encoded by the endogenous metJ gene and has L-methionine productivity, activity of intracellular homoserine transsuccinylase encoded by the metA gene of a *Escherichia* bacterium is increased compared to an unmodified *Escherichia* bacterium by increasing copy number of the metA gene including its own promoter, or replacing the native promoter with a stronger promoter, and the bacterium comprises at least one characteristic selected from the group consisting of:

(a) exhibits reduced activity of intracellular S-adenosylmethionine synthetase encoded by the endogenous metK gene as compared to an unmodified *Escherichia* bacterium;

(b) exhibits L-threonine auxotrophy;

(c) exhibits enhanced activity of intracellular cystathionine γ-synthase encoded by the metB gene of a *Escherichia* bacterium and enhanced activity of intracellular aspartokinase-homoserine dehydrogenase II encoded by the metL gene of a *Escherichia* bacterium as compared to an unmodified *Escherichia* bacterium by increasing copy number of each of the genes including their own promoters, or replacing the native promoter with a stronger promoter; and (d) has a homoserine transsuccinylase for which concerted inhibition by L-methionine and S-adenosylmethionine is desensitized, wherein the homoserine transsuccinylase comprising the amino acid sequence of SEQ ID NO: 26 contains at least one amino acid replacement wherein said at least one amino acid replacement is independently selected from the group consisting of replacement of the amino acid residue Arg-27 with cysteine, replacement of the amino acid residue Ile-296 with serine, and replacement of the amino acid residue Pro-298 with leucine.

2. The method according to claim 1, wherein the bacterium is *Escherichia coli*.

3. The method according to claim 1, wherein the bacterium comprises at least the characteristic (a).

4. The method according to claim 1, wherein the bacterium comprises at least the characteristic (b).

5. The method according to claim 1, wherein the bacterium comprises at least the characteristic (c).

6. The method according to claim 1, wherein the bacterium comprises at least the characteristic (d).

7. The method according to claim 1, wherein the bacterium comprises the characteristics (a) and (b).

8. The method according to claim 1, wherein the bacterium comprises the characteristics (a) and (c).

9. The method according to claim 1, wherein the bacterium comprises the characteristics (a) and (d).

10. The method according to claim 1, wherein the bacterium comprises the characteristics (b) and (c).

11. The method according to claim 1, wherein the bacterium comprises the characteristics (b) and (d).

12. The method according to claim 1, wherein the bacterium comprises the characteristics (c) and (d).

13. The method according to claim 1, wherein the bacterium comprises the characteristics (a), (b), and (c).

14. The method according to claim 1, wherein the bacterium comprises the characteristics (a), (b), and (d).

15. The method according to claim 1, wherein the bacterium comprises the characteristics (a), (c), and (d).

16. The method according to claim 1, wherein the bacterium comprises the characteristics (b), (c), and (d).

17. The method according to claim 1, wherein the bacterium comprises the characteristic (a), (b), (c), and (d).

18. The method according to claim 1, wherein the activity of intracellular S-adenosylmethionine synthetase is reduced due to that the bacterium has S-adenosylmethionine synthetase which contains amino acid substitution which is selected from the group consisting of replacement of the amino acid residue Ile-303 with leucine, replacement of the amino acid residue Val-185 with glutamic acid, and replacement of amino acid residues 378-384 with the amino acid sequence of SEQ ID NO: 29, respectively in the amino acid sequence of SEQ ID NO: 18.

19. The method according to claim 3, wherein the activity of intracellular S-adenosylmethionine synthetase is reduced due to that the bacterium has S-adenosylmethionine synthetase which contains amino acid substitution which is selected from the group consisting of replacement of the amino acid residue Ile-303 with leucine, replacement of the amino acid residue Val-185 with glutamic acid, and replacement of amino acid residues 378-384 with the amino acid sequence of SEQ ID NO: 29, respectively in the amino acid sequence of SEQ ID NO: 18.

20. The method according to claim 1, wherein the L-threonine auxotrophy is due to deletion of the thrBC genes.

21. The method according to claim 4, wherein the L-threonine auxotrophy is due to deletion of the thrBC genes.

* * * * *